(12) United States Patent
Aphinyanaphongs et al.

(10) Patent No.: US 8,275,772 B2
(45) Date of Patent: Sep. 25, 2012

(54) CONTENT AND QUALITY ASSESSMENT METHOD AND APPARATUS FOR QUALITY SEARCHING

(76) Inventors: Yin Aphinyanaphongs, Nashville, TN (US); Constantin Aliferis, New York, NY (US)

( * ) Notice: Subject to any disclaimer, the term of this patent is extended or adjusted under 35 U.S.C. 154(b) by 935 days.

(21) Appl. No.: 12/195,062

(22) Filed: Aug. 20, 2008

(65) Prior Publication Data

US 2009/0077068 A1  Mar. 19, 2009

Related U.S. Application Data

(63) Continuation-in-part of application No. 11/129,388, filed on May 16, 2005, now Pat. No. 7,529,737.

(60) Provisional application No. 60/570,879, filed on May 14, 2004.

(51) Int. Cl.
*G06F 7/00* (2006.01)
*G06F 17/30* (2006.01)

(52) U.S. Cl. ........................ 707/738; 707/740
(58) Field of Classification Search ............... 707/738, 707/740
See application file for complete search history.

(56) References Cited

U.S. PATENT DOCUMENTS

| | | | |
|---|---|---|---|
| 6,128,608 A | 10/2000 | Barnhill | |
| 6,789,069 B1 | 9/2004 | Barnhill | |
| 6,976,207 B1 * | 12/2005 | Rujan et al. | 715/234 |
| 7,240,038 B2 | 7/2007 | Hitt | |
| 7,249,312 B2 * | 7/2007 | Jasper et al. | 715/205 |
| 2003/0016250 A1 * | 1/2003 | Chang et al. | 345/810 |
| 2003/0144996 A1 * | 7/2003 | Moore, Jr. | 707/3 |
| 2005/0120006 A1 | 6/2005 | Nye | |
| 2005/0154686 A1 | 7/2005 | Corston | |
| 2005/0228783 A1 | 10/2005 | Shanahan | |
| 2007/0239638 A1 | 10/2007 | Zhuang | |
| 2007/0294223 A1 | 12/2007 | Gabrilovich | |

\* cited by examiner

*Primary Examiner* — Mariela Reyes
(74) *Attorney, Agent, or Firm* — Laurence Weinberger

(57) ABSTRACT

A computer-based process retrieves information organized in documents containing text and/or coded representations of text. The process involves obtaining and labeling a selected set of documents based on content quality, and extracting and representing features from each document in the selected set. The extracted and selected features are modified, and models are constructed using parametric learning algorithms. The constructed models are capable of assigning a label to each document. The model parameters are instantiated using a first subset of the selected set of documents. Parameters are chosen by validating the corresponding model against at least a second subset of the full document set. The constructed models also are capable of assigning labels to similar documents outside a selected subset not previously given to the process of model construction.

42 Claims, 8 Drawing Sheets

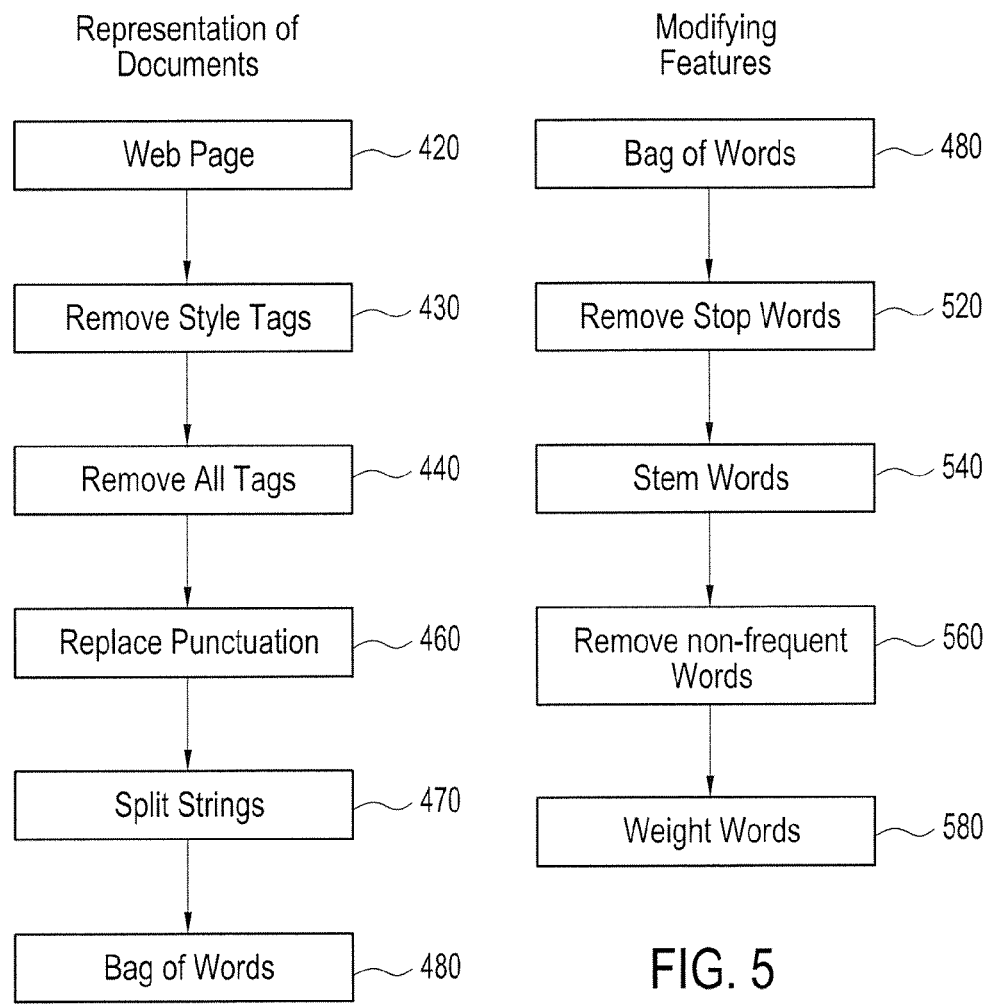

1

CONTENT AND QUALITY ASSESSMENT METHOD AND APPARATUS FOR QUALITY SEARCHING

CROSS-REFERENCE TO RELATED APPLICATIONS

This application is a continuation in part of the application Ser. No. 11/129,388 filed May 16, 2005 now U.S. Pat. No. 7,529,737, the entire disclosure of which is incorporated herein by reference. application Ser. No. 11/129,138 claims the benefit of U.S. Provisional Appl. No. 60/570,879 filed May 14, 2004, the entire disclosure of which is incorporated herein by reference.

BACKGROUND OF THE INVENTION

Today, people search the internet to obtain information on every known topic. This is largely because information can be disseminated at an unparalleled rate and accessed so easily on the internet. Unfortunately not all the information published on the internet is correct. Nor are there ratings or applied standards to every website to alert people that information on the website may be incorrect. This leads to many people relying on incorrect information. In fact, certain groups of people may be more susceptible to relying on incorrect information found on the internet. For example, it has been reported that cancer patients are susceptible to relying on unproven cancer treatments that are posted on the internet.

Unproven cancer treatments are known as quackery with the quacks promoting them defined as untrained people who pretend to be physicians and dispense medical advice and treatment. The internet allows quacks to advocate inaccurate and unproven cancer treatments. These unproven treatments have had adverse outcomes and in some extreme cases the treatments have proven fatal. Studies have reported that a large majority of cancer patients used at least one unproven treatment, while some cancer patients have gone as far as purchasing unconventional medical therapies off of the internet.

There are several manual methods used to alert cancer patients to unproven cancer treatments on the internet. The Health-on-the-Net Foundation advocates self regulation of health related web pages. The foundation applies strict criteria to web pages and grants them a seal of approval if they pass. In another approach, experts produce rating tools that allow consumers to rate web pages so that future users can have a basis for evaluating a webpage. Another method is the manual review of individual web pages that are published either in print or electronically.

Unfortunately, all these methods have drawbacks: self-regulation relies on knowledge of the certification and a vigilant public to report failing web pages; rating tools are dependent on a knowledgeable public to apply, they are difficult to validate, time consuming to produce, and do not always produce consistent ratings; manual review suffers from limits in reviewer time and selection of web pages to review.

To try to solve these issues automated approaches have been developed to identify high quality web pages. One approach is to evaluated web pages content by combining a score measuring quality proxies for each page. Although this algorithm can discriminate between desirable and undesirable web pages, the algorithm does not measure content quality directly and some of the criteria used may not correlate with true content quality. In addition, Google has become a de facto standard for identifying and ranking web pages. Researchers have explored the use of the Page Rank score in assessing the quality of health web pages and found that it is not inherently useful for discriminating or helping users to avoid inaccurate or poor information.

What is needed is an automated approach for evaluating web pages content that measures the content quality directly and identifies high and low quality pages.

BRIEF SUMMARY OF THE INVENTION

In accordance with the invention there is provided a method of determining the content quality of documents. A computer based process for filtering information according to the content quality including the step of obtaining a selected set of documents and labeling each document based on content quality. Features are extracted and represented from each document and then modified. Models that can label documents according to content quality are constructed using a pattern recognition algorithm. The parameters for the models are instantiated using a first subset of the selected set of documents. The parameters are chosen by validating the corresponding model against a second subset of the selected set of documents. Wherein during a search for related documents, the validated model labels the search result documents based on content quality.

The steps of, instantiating the model to determine the parameters, and verifying the model, can be performed iteratively. In addition, a third subset of documents, mutually exclusive of the first and second subsets, is applied to the model to evaluate performance. This third subset can be applied iteratively. The labeled documents can then be displayed to the user or negatively labeled documents can be excluded from the search.

BRIEF DESCRIPTION OF THE DRAWINGS

FIG. 4 illustrates the process of representing a webpage for use in generating models according to an exemplary embodiment of the present invention;

FIG. 5 illustrates the process of modifying a webpage's features for use in generating models according to an exemplary embodiment of the present invention;

DETAILED DESCRIPTION OF THE INVENTION

Figure 1:
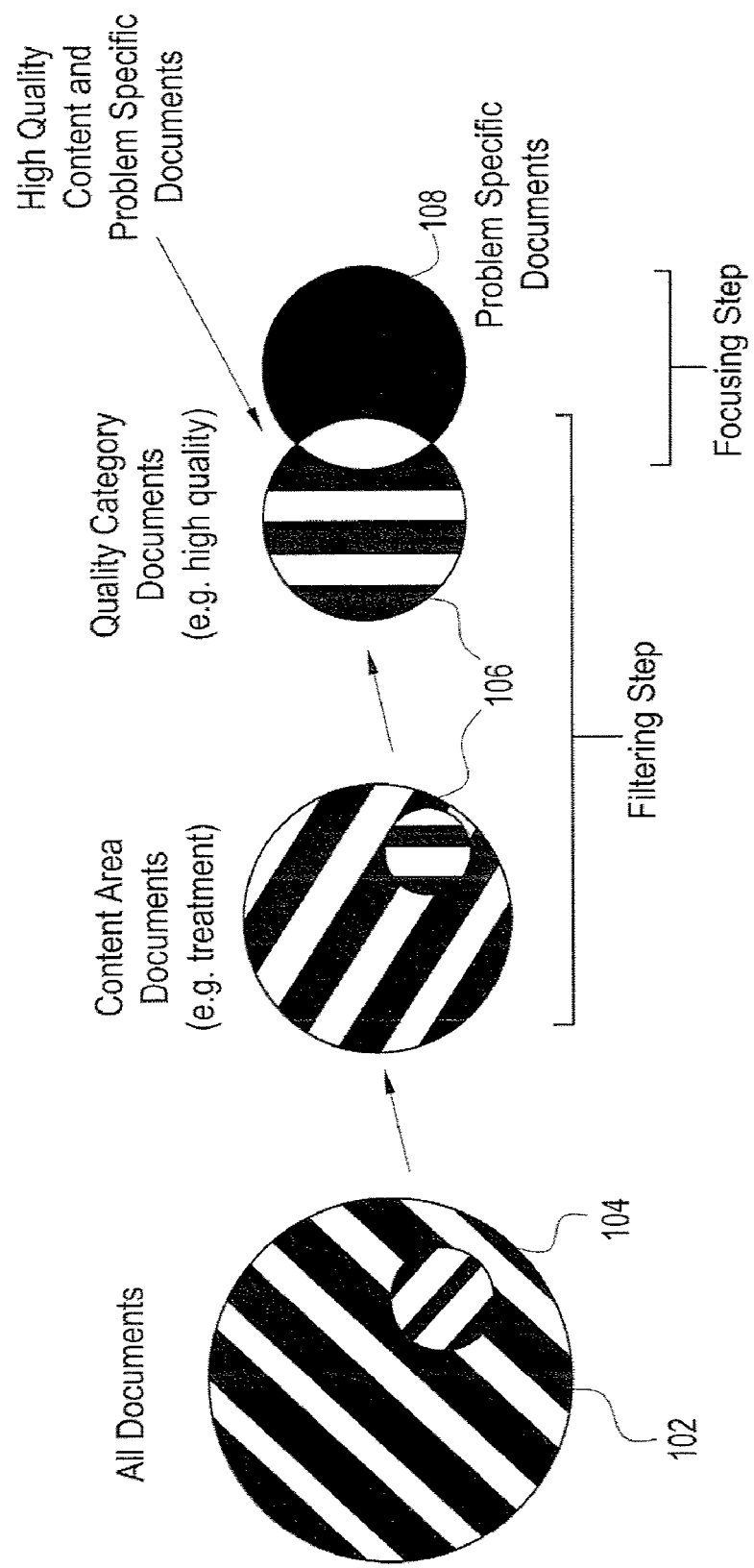
FIG. 1 illustrates high-level functionality of an exemplary embodiment of the present invention.

Referring initially to FIG. 1, high-level functionality is illustrated in an exemplary embodiment of the invention. The invention provides filtering models, and methods to build filtering models that extract from the space of all available documents 102 sets of content-area documents 104 that satisfy specific criteria. The sets may be selected or further refined by extracting smaller sets of category documents 106 that may be either quality documents (e.g., describing cancer treatment that are of high methodological quality) or low quality documents (e.g., describing cancer treatment that are of low methodological quality).

The invention is further exemplified by use of the filtering models as components in an information-retrieval system, for example, which may carry out problem-focusing and user-interfacing functions by further extracting problem-specific subsets 108 of the filtered-document sets (e.g., if the problem is to treat a patient with colon cancer, the subset returned is the intersection of two classes of documents: all documents mentioning treatments of colon cancer, and high-quality treatment-related articles).

The filtering models can but do not necessarily assign labels or classification. The filtering models typically return a ranking score whose semantics may imply that the higher the score the more likely the document is to belong to a specific classification or category (one of which, in the example above, would be high quality, treatment-related articles).

Figure 2:
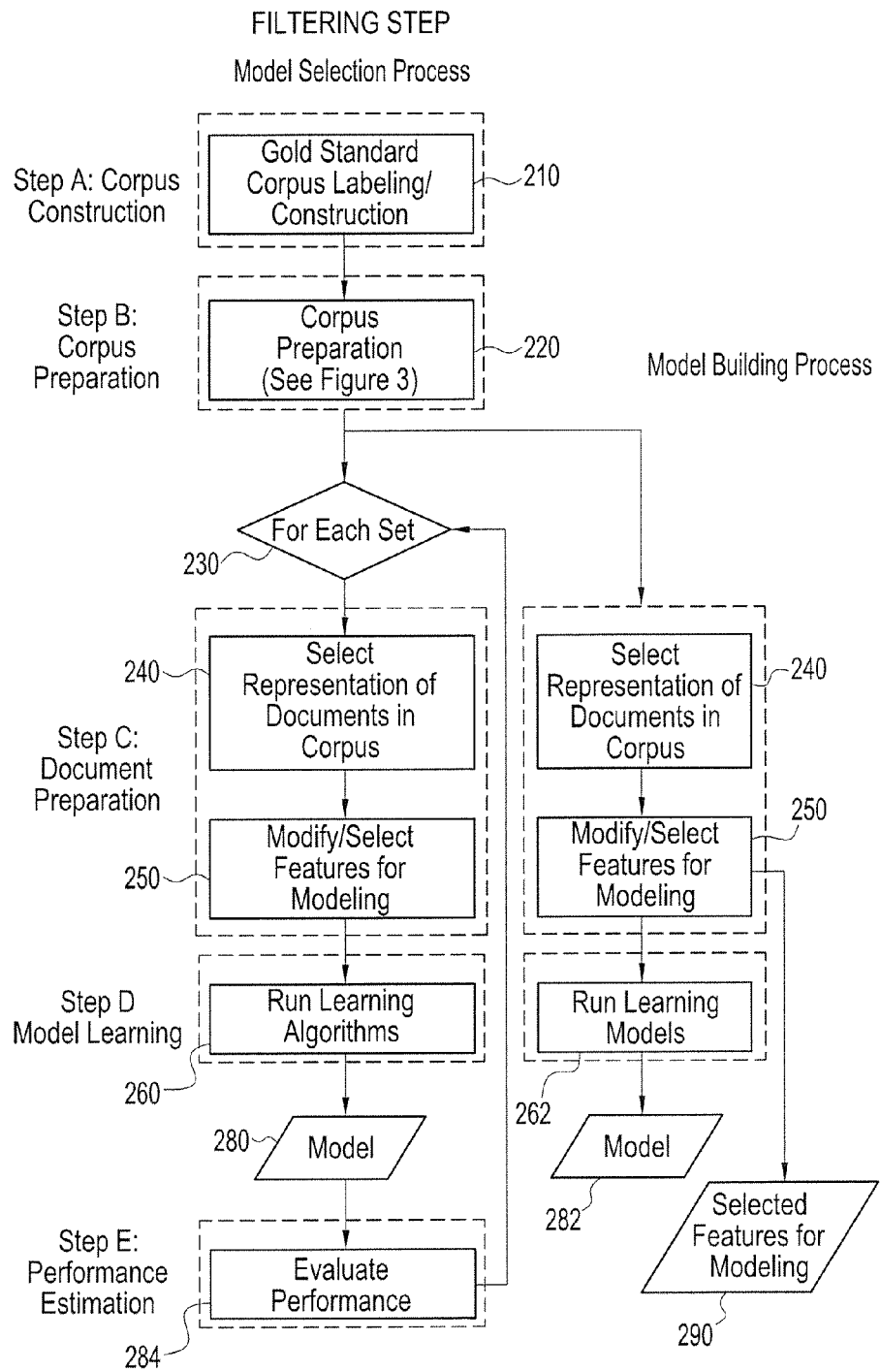
FIG. 2 summarizes the process of creating filtering models according to an exemplary embodiment of the present invention.

Process and Apparatus to Create Filtering Models:

Referring now to FIG. 2, the process of creating filtering models according to an exemplary embodiment of the invention can be summarized as follows:

Corpus Construction

First, during corpus construction 210, a specific subject is selected for which filtering is desired to determine the quality of documents in that subject area. An example of documents with specific content would be "web pages with cancer treatment claims." Typically a more discrete and narrow subject area allows a filtering model to better determine the quality of the documents. The documents that fall within the desired subject area are classified into at least two categories according to their quality. The two categories are high quality and low quality. More categories can be chosen based on different levels of quality. The quality categories are assigned labels, and in the case of two categories, the categories are generically labeled as negative and positive. Typically a certain quality level is desired to be identified and a label designating the desired quality is referred to as the target label. The target label documents are given a positive label. For example, if web pages with cancer treatment claims with a low quality or in essence web pages with unproven cancer treatment claims are desired to be identified, they are given a positive label. Web pages with proven cancer treatment claims are given a negative label. However, a negative label could be given either category since the label name is simply nomenclature used to identify the quality of documents within a category.

The labeling of the corpus documents 210 is dependent on how the target-label is defined and on how the finished model is to characterize documents. The choice and quality of the corpus 210 will also determine the specific focus and applicability of the model developed. In addition, the specification of labels for the corpus 210 need not be dichotomous. Labels from several gold standards can be combined, and models built to differentiate amongst several labels. As such, the labels of the gold standard 210 need not be binary but may be of multiple categories. Also, the corpus labels can be specified by a single user and applied only for that user's benefit.

After the specific subject area and labels are chosen, a gold-standard set of documents ("corpus") 310 is selected. The corpus documents 310 are a selected subset of all documents that have specific criteria to fall within the chosen subject area. In an exemplary embodiment the corpus contains documents with content about cancer treatment claims. The corpus 310 needs to contain at least one document for each level of quality that will be labeled. However, ideally the corpus will contain approximately equal amounts of documents for each level of quality being labeled.

Further, for a pattern recognition algorithm to produce a filtering model that classifies documents with a reasonable degree of accuracy the corpus 310 should be sufficiently large. A smaller corpus 310 would still produce a model; however the model may not be as accurate as a model that was trained using a larger corpus 310.

After identifying the documents, the documents need to be collected and stored. An exemplary embodiment of a corpus 310 is web pages that discuss cancer treatments of high and low qualities. The web pages are selected through a search algorithm that uses specific terms to identify pages that discuss cancer treatments. The web pages are then downloaded using a python script or some other known scripting programming language and saved in raw HTML format. A corpus 310 could also be formed with articles that are taken from journals. These articles or other documents could be obtained in Word document form. After obtaining the documents, each document from the corpus 310 is then given a label based on quality. The labels could have been determined previously or after selection of the documents.

Corpus Preparation

Figure 3:
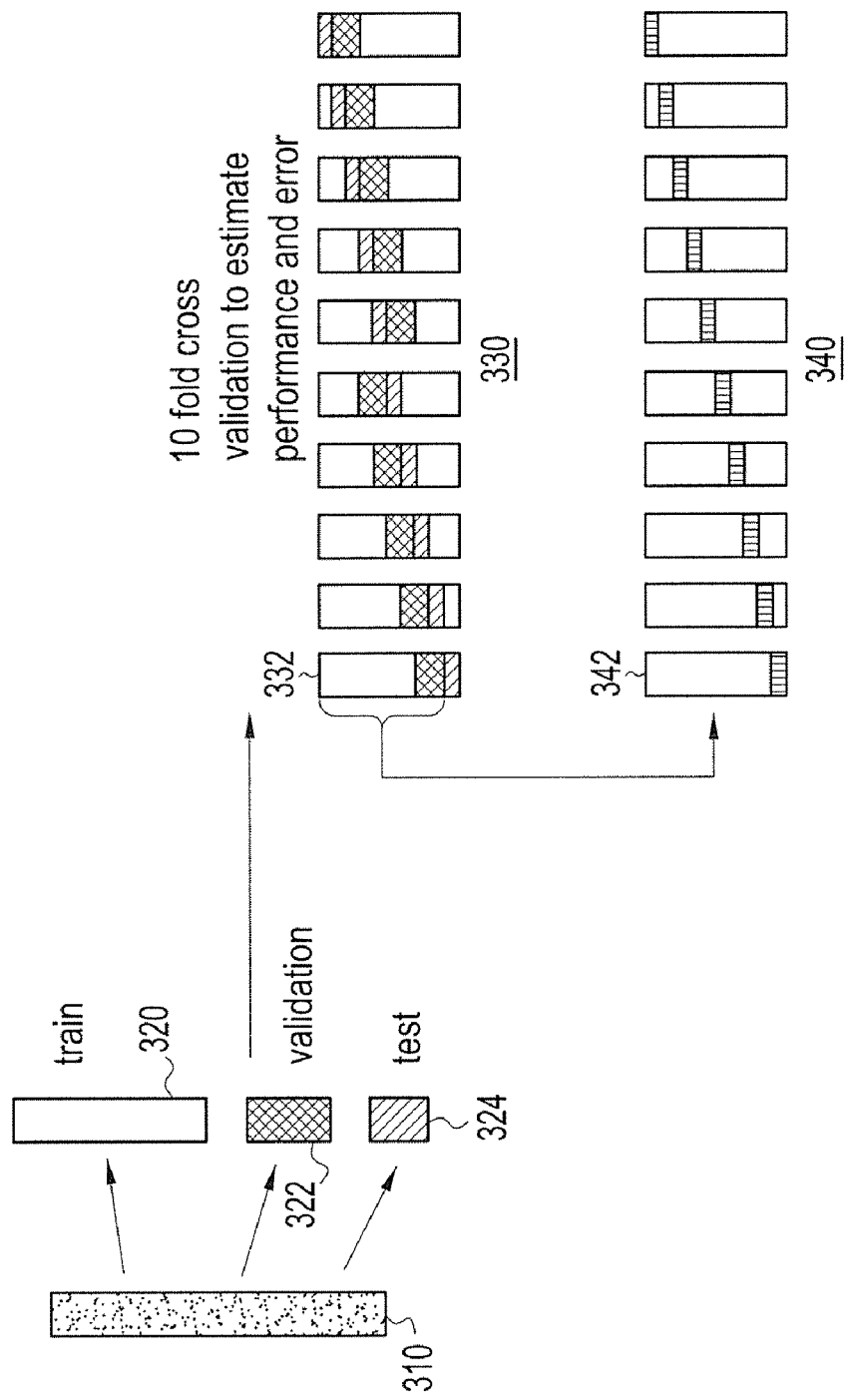
FIG. 3 illustrates one example of how the cross-validation procedure operates according to an exemplary embodiment of the present invention.

Next, during corpus preparation 220 the labeled corpus documents 310 are split into n-fold cross validation sets 330, where each individual set 332 is split into categories. Each individual set 332 contains all the corpus documents 310. The number n of the n-fold cross validation sets 330 is chosen based on the frequency of positive or negative labeled documents as determined during corpus construction 210. The choice for n should allow for sufficient documents from each category in each individual set 332. However, the number of sets used may range from 1 to the number of documents in the corpus 310. An exemplary embodiment of the cross-validation procedure illustrated in FIG. 3 is one in which the corpus 310 is split into ten individual sets 332. The individual sets 332 are distinguished from one another according to which documents of the corpus 310 are placed in certain categories as illustrated in FIG. 3. The data-splitting procedure during corpus preparation 220 is done to ensure that the filtering models selected and their estimated performance is not a by-product of a particularly favorable or bad split of the data.

Corpus Preparation to Estimate Performance

The corpus documents 310 in an individual set 332 are divided into three categories during cross validation to estimate performance and error. The three categories are the training category 320, validation category 322, and test category 324. The union of the training category 320, validation category 322, and test category 324, is the complete corpus 310 and form an individual set 332. Each category should contain approximately the same proportion of negative and positive documents as the entire corpus 310. The training category documents 320 are used to build filtering models, the validation category documents 322 are used to optimize any specific parameters for the pattern recognition algorithms that build the filtering models, and the test category documents 324 are used to measure the performance of the best model on previously unseen documents.

The documents from the test category 324 from each set 332 are mutually exclusive of the documents of the test category in the nine remaining individual sets 332. As such, the union of the documents from the test category 324 from each set 332 is all the corpus documents 310. For example if one-hundred corpus documents where made into ten sets, then each set 332 would have ten documents in their training category. One set 332 of the ten sets 330 would have documents 1-10 in its testing category 324, another set 332 of the ten sets 332 would have documents 11-20 in its testing category 324. The remaining documents would be divided into the remaining eight sets 332 as described above. Having mutually exclusive testing categories documents 324 allows for final performance estimates to be unbiased because each document is used only once to estimate performance of a single filtering model that is built by using training category documents 320 exclusively. Once documents are assigned to a testing category 324 in an individual set 332, the remaining documents are split into the training category 320 and validation category 322. An example of the split for a corpus 310 of one-hundred documents is having ten documents of the corpus 310 in the testing category 324, nine documents of the corpus 310 in the validation category 322 and eighty-one documents of the corpus 310 in the training category 320.

Corpus Preparation for Filtering Models

The process of generating the best-performance filtering model is distinct from the process of cross validation to estimate performance and error of unseen cases. While the corpus documents 310 are split into n-fold cross validation sets 330 where each individual set 332 is split into categories as described above, the process of generating the best performance filtering model only requires a validation category 322 and training category 320. No test category 324 is needed in generating the best performance filtering model 282. As such, the training category 320 sample size is increased for creating the final best performance filtering model 282 because no documents are placed in the testing category 324.

The assigning of documents of the corpus 310 to a category in an individual set 332 to generate a filtering model is done in a similar manner as describe above with respect to generating a model to estimate future performance. To create a filtering model only, the documents of the corpus 310 in a set 332 that would have comprised the test category 324 instead comprise the validation category 322 as described above. The remaining documents of the corpus 310 are placed in the training category 320. Thus, the union of the training category 320 and the validation category 322 is the complete corpus 310 for each individual set 332.

Document Representation

Within each individual set 332 a representation is chosen for each document of the corpus 310. One such representation used specifically in an exemplary embodiment of the invention is a "bag of words" approach where each web page is split into individual words (also called "features" or "terms"). Referring now to FIG. 4, which shows a process, according to an exemplary embodiment, where a webpage is represented as a bag of words 480 during document representation 240. Before the document can be represented as a bag of words 480 the document must first be obtained. In the case of a webpage 420 the HTML code of the webpage must be obtained. A python script is used to access the webpage 420 and download and store the HTML code for the webpage 420 as described in corpus construction 210. Other various programming languages or scripts languages could be used to download and store the HTML code of a webpage 420. Once the HTML code of the webpage 420 is obtained, all the content between the style and script tags of the HTML are removed at step 430. Following the removal of the content between the style and script tags at step 430; all HTML tags are removed at step 440. At step 460 all punctuation is removed and replaced with a space. Step 470 then parses the string of words that is left into individualized words. The result is a bag of words 480 that represents just the word content of the webpage.

Similar steps can be taken when dealing with documents to parse the document into a bag of words 480. Of course, the representation of documents does not have to be through a bag of words 480; each document could be pre-processed by natural language processing techniques. These techniques include negation detection, sense disambiguation, automatic mapping to the UMLS (or other appropriate canonical language). In addition, several existing representations that preserve term order may be employed such as ordered term lists, term positions, HMMs, context-sensitive classifiers, transformation-based learning, or stochastic grammars.

Once the documents of the corpus 310 have been converted into a bag of words 480 or represented in another manner, the features of the webpage are modified and/or selected for modeling during feature modification 250. FIG. 5 shows the steps taken in an exemplary embodiment of the invention to modify and select the features of the webpage for modeling. The process shown in FIG. 5 begins with a bag of words 480 produced during document representation 240. The bag of words is processed by removal of stop words in step 520. Stop words are words such as "the," "a," "other," etc. that do not add semantic value to a classification. Once all stop words are removed in step 520, the remaining words are stemmed in step 540. Stemming reduces words to their roots. For example the terms "randomly," "randomness," and "randomize" all describe a similar state yet each word would be recognized by a model producing algorithm as a different word. When the words are stemmed they are all reduced to the word "random." Thus, stemming increases the effective sample be encoding the term "random" three times rather than encoding the other three terms once. The Porter stemming algorithm is used to stem words, however other stemming algorithms could effectively be used to accomplish the stemming of step 540.

The frequency of the remaining words is then determined in step 560 and words that appear in less than three documents are removed. The webpage has thus been reduced from HTML code to a group of stemmed words that does not include infrequent words or stop words. After having determined the words that will be used to produce the model by following the above steps the words are encoded into a numerical value in step 580. To encode the words with a numerical value a log frequency with redundancy algorithm is used. The log frequency with redundancy algorithm weights words based on their usefulness in making a classification. Words that appear frequently in many documents are assumed to be less helpful in classification then more selective words that appear in fewer documents. This weighting algorithm was chosen due to its superior classification performance in the text categorization literature. Other weighted schemes known in the art could be used as well.

The entire text of the document does not need to be selected to represent the document. For example, a variation may include using only the title and abstract terms from a document. Also, the representation of a document or webpage may be constructed by other locations of occurrence within the document itself. Also, other factors can be used in building the filtering model. Information such as citations, journal, authors, home institution, etc., can be used along with the contents of the documents as predictors to building the filtering models.

What's more, document representation 240 and feature modification 250 can be run on each individual set 332 or different forms of document representation 240 and feature modification 250 as described above can be run on each set 332. Further, different preparation of the documents through document representation 240 and feature modification 250 can be done on the different categories in a set 332. However, if the same document representation 240 and feature modification 250 are run on each individual set then document representation 240 and feature modification 250 can be run on the entire corpus 310 before the corpus 310 is split into sets during corpus preparation 210. The above described processes of document representation 240 and feature modification 250 can be done manually or they can be automated.

Pattern Recognition Algorithm

The processes described above are done to enable the pattern recognition algorithm to produce the best model. A pattern recognition algorithm takes the modified bag of words or other representation of the documents and learns to distinguish between low and high quality documents based on information in the documents and the labels given the documents during corpus construction 210. The pattern recognition algorithm used in the exemplary embodiment is the Support Vector Machine (SVM) classification algorithm. The SVM calculates maximal margin hyperplane(s) separating two or more classes of data. The basic algorithm is reproduced below where K represents a kernel and C a penalty parameter:

$$\min_{a} \frac{1}{2} \sum_{i=1}^{m} \sum_{j=1}^{m} y_i y_j a_i a_j K(x_i, x_j) - \sum_{i=1}^{m} a_i$$

where $$\sum_{i=1}^{l} y_i a_i = 0; C \geq a_i \geq 0; i = 1, \ldots, m$$

The SVM algorithm used was implemented in code with a polynomial kernel. Other common kernels that could have been used include RBF and two layer neural network kernels. The polynomial kernel used is reproduced below:

$$K(x_i, x_j) = (x_i \cdot x_j + 1)^d$$

Two parameters in the SVM algorithm need to be optimized for each corpus 310 that is being used to develop a filtering model. The parameters are the penalty parameter C and the degree d of the polynomial kernel. Before the parameters can be optimized a finite range of parameters must be selected. In an exemplary embodiment parameter C is construed over the range $\{0.1, 1, 2, 5, 10\}$. The degree d of the polynomial kernel is limited to the range $\{1, 2, 5\}$. The ranges were selected based on previous research. Larger ranges can be used, however the larger range will increase the time required to generate a filtering model. The selection of parameters from a range allows for the SVM algorithm to be fine-tuned to allow for the best model to be developed based upon a corpus 310. Because of the range of possible parameters various combinations of the parameters C and d exist. Thus, each individual combination of the parameters is therefore used to develop a model and then validated to determine the optimal combination for that corpus 310.

Figure 6:
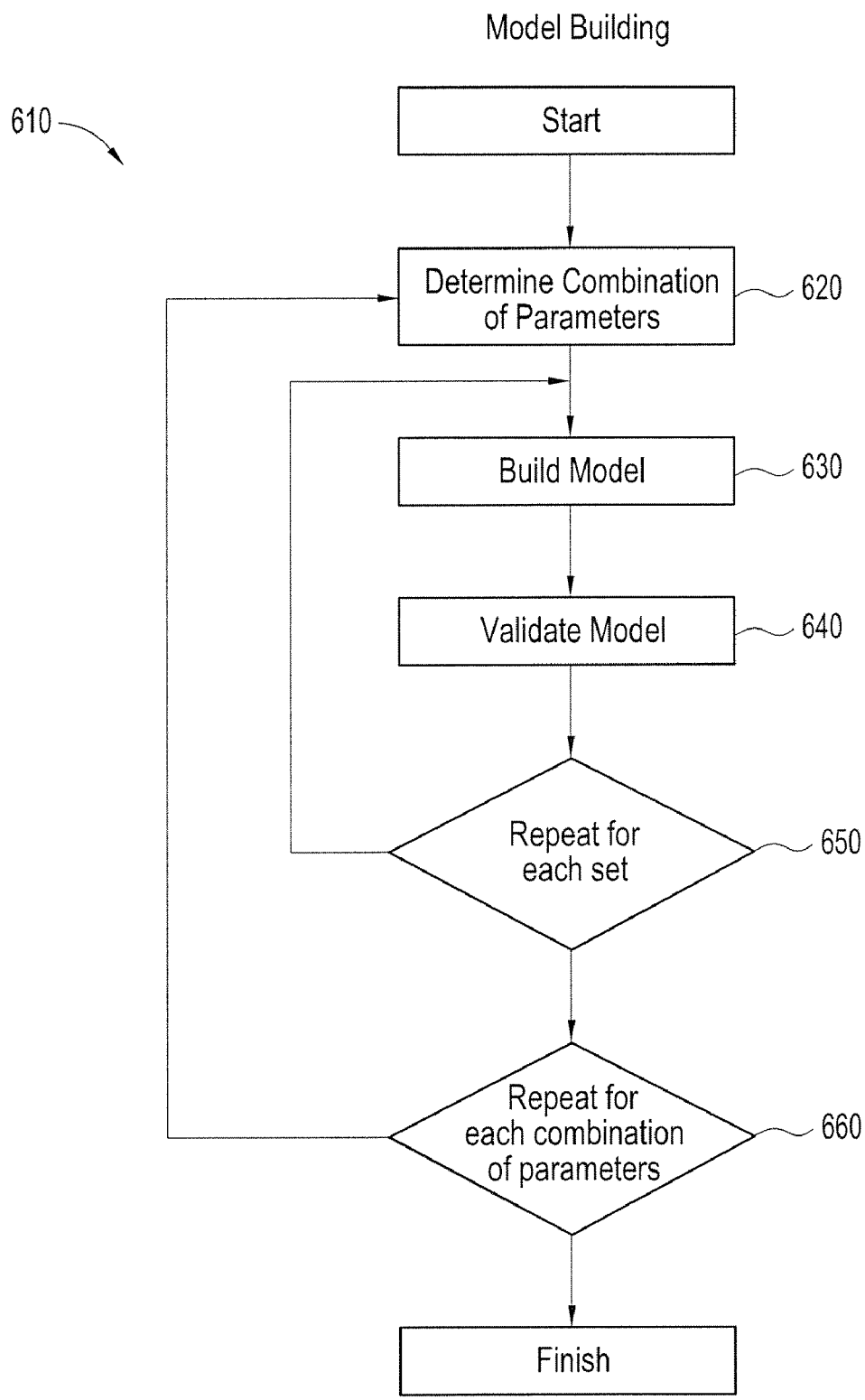
FIG. 6 illustrates the process of cross-validation used to generate models according to an exemplary embodiment of the present invention.

Referring now to FIG. 6 that shows the process 610 of selecting the optimal combination of parameters that is typically referred to as cross validation. A single combination of parameters C and d are selected in step 620. The SVM algorithm is then implemented with the combination of parameters. The algorithm generates a filtering model using the training category 320 documents from a set 332 in step 630. The newly generated model from step 630 is then validated in step 640 using the validation category 322 documents from the same set 332 used in step 630. The performance of the model generated from the combination of parameters is recorded. The performance is based on how many of the documents from the validation category 332 the model labels correctly. In step 650, steps 630 and 640 are then repeated on each of the individual sets 332 created during corpus preparation 220. From the exemplary embodiment with ten different individual sets 332, steps 630 and 640 are repeated ten times. The recorded performance from each set 332 of the total sets 330 are averaged or combined for a composite performance measure for that combination of parameters. In step 660, the process of determining the composite performance measure for a combination of parameters is then repeated for each individual combination of parameters C and d.

Model Building Process

The process of building a best performance filtering model is shown in FIG. 2. A corpus is selected during corpus construction 210 and then divided into sets during corpus preparation 220. The set 332 made during corpus preparation 220 includes only a training category 320 and a validation category 322. A testing category 324 does not need to be used in the process of building an optimal filtering model. The manner of representing the web pages or documents of the corpus 310 is then selected during document representation 240 and modified during feature modification 250. The classification algorithm is then run during best model construction 262 as described in process 610. The model with the combination of parameters with the highest composite performance measure is then selected as the best performance model 282.

The use of cross validation as described above when making a filtering model helps to ensure that the models are sufficiently general to perform will on data that the filtering model has not seen before. The output of the models produced is non-probabilistic. However, the output of a filtering model developed according to the method described above can be converted to probabilities using standard probability fitting methods. Clustering methods can also further organize the results from the filtering models into coherent subgroups of documents; automatic identification of prominent keywords can characterize the contents of each automatically-created cluster.

During feature modification 250 of the filtering model generating process, selected features can be obtained. These features are useful as follows:

(a) To explain to the end user why the content-quality filters label documents the way they do (which may be infeasible or computationally intractable with "black box" classifiers such as support vector machines (SVMs) and neural networks (NNs)).

(b) To convert the filter models to queries that can be used by standard Boolean-query search-interfaces.

(c) To examine hidden biases of the creators of the gold standard corpora 310.

Model Performance Estimation

The process of determining a performance estimate of a filtering model developed by the corpus 310 is shown in FIG. 2. A corpus is selected during corpus construction 210 and then divided into sets during corpus preparation 220. The individual sets 332 made during corpus preparation 220 include a training category 320, validation category 322 and the testing category 324. The process of selecting the documents from the corpus 310 for the testing category 324 in each individual set 332 was explained previously. The manner of representing the web pages or documents of the corpus 310 is then selected during document representation 240 and modified during feature modification 250. The optimal combination of parameters for the classification algorithm needs to be determined for the specific group of documents in the training category 320 for the individual set 332.

One way to determine the optimal combination of parameters is to follow a process similar to process 610 in which a filtering model is built for each combination of parameters using the documents in the training category 320. The model is then validated by the documents in the validation category 322. The filtering model with the best performance is developed during model estimate construction 260 and then the estimate filtering model 280 is evaluated during model performance estimation 284 using the documents from the testing category 324. The estimate filtering model 280 is evaluated during the model performance estimation 284 by determining if the model correctly labeled the test category documents 324. The above process and evaluation is repeated 230 for each set 332 of the group of sets 330 and the average performance of the group of set 330 represents a performance estimate for a future best filtering model 262 developed from that corpus. The estimate filtering model 280 developed with the best performance in the above process can then be used as a best performance filtering model 282 or a best performance filtering model 282 can be created separately as described in the model building process section.

Alternatively, a slightly different method called nested cross validation can be used to estimate the performance of the model. Nested cross validation differs from the method described above with respect to determining the optimal combination of parameters. Using nested cross validation helps to ensure that the performance estimates do not over fit the data. To perform nest cross validation the method from above is followed through feature modification 250.

During model estimate construction 260 when performing nested cross validation the documents from the training category 320 and the validation category 322 are treated as if they were a whole corpus 310. The training category 320 and the validation category 322 documents of one individual set 332 are made into the same number of subsets 340 as sets 330 that were created during corpus preparation 220. Each individual subset 342 of the subsets 340 contains a training category 320 and a validation category 322. The same procedure as described previously is used in determining which documents are placed in the validation category so that the union of all the validation categories 322 of the subsets 342 is the union of the training category 320 and validation category 322 of one individual set 332. For example, if the corpus contained one-hundred documents and was split into ten sets then ten documents would be placed in the testing category 324 for each individual set 332. Then the remaining ninety documents would be divided with nine documents belonging to the validation category 322 and eighty-one belonging to the training category 320. Each individual subset 342 would have nine documents in the validation category 332 that are mutually exclusive of the documents in the validation category 332 of the other nine subsets 342.

The pattern recognition algorithm is then run in process 610 as described in FIG. 6 and above in the pattern recognition algorithm section to determine the best combination of parameters. Once the best combination of parameters is determined for a subset 342 then the documents from the validation category 322 and the training category 320 are combined to form a new larger training category 320 that includes all the documents in the set 332 besides the documents in the testing category. Following from the example above the new training category 320 of a set 332 would have ninety documents.

The new training category 320 documents are then used to train a new filtering model using the pattern recognition algorithm with the best combination of parameters found for that set 332. The model is evaluated in step 284 using the testing category 324 documents and the performance is recorded. Each set 332 of the group of sets 330 follows the nest cross validation process described and records the set's 332 performance. The average performance of the sets 330 represents a performance estimate for a model developed from that corpus. The final performance estimate obtained by this procedure will be unbiased because each original testing set is used only once to estimate performance of a single model that was built using training data exclusively. The model developed with the best performance can then be used as the final best performing model 282 or a best performing model 282 can be created as described above. The cross validation and nested cross validation used in the above examples could also be accomplished via bootstrapping, leave-one-out, or holdout methods.

Figure 7:
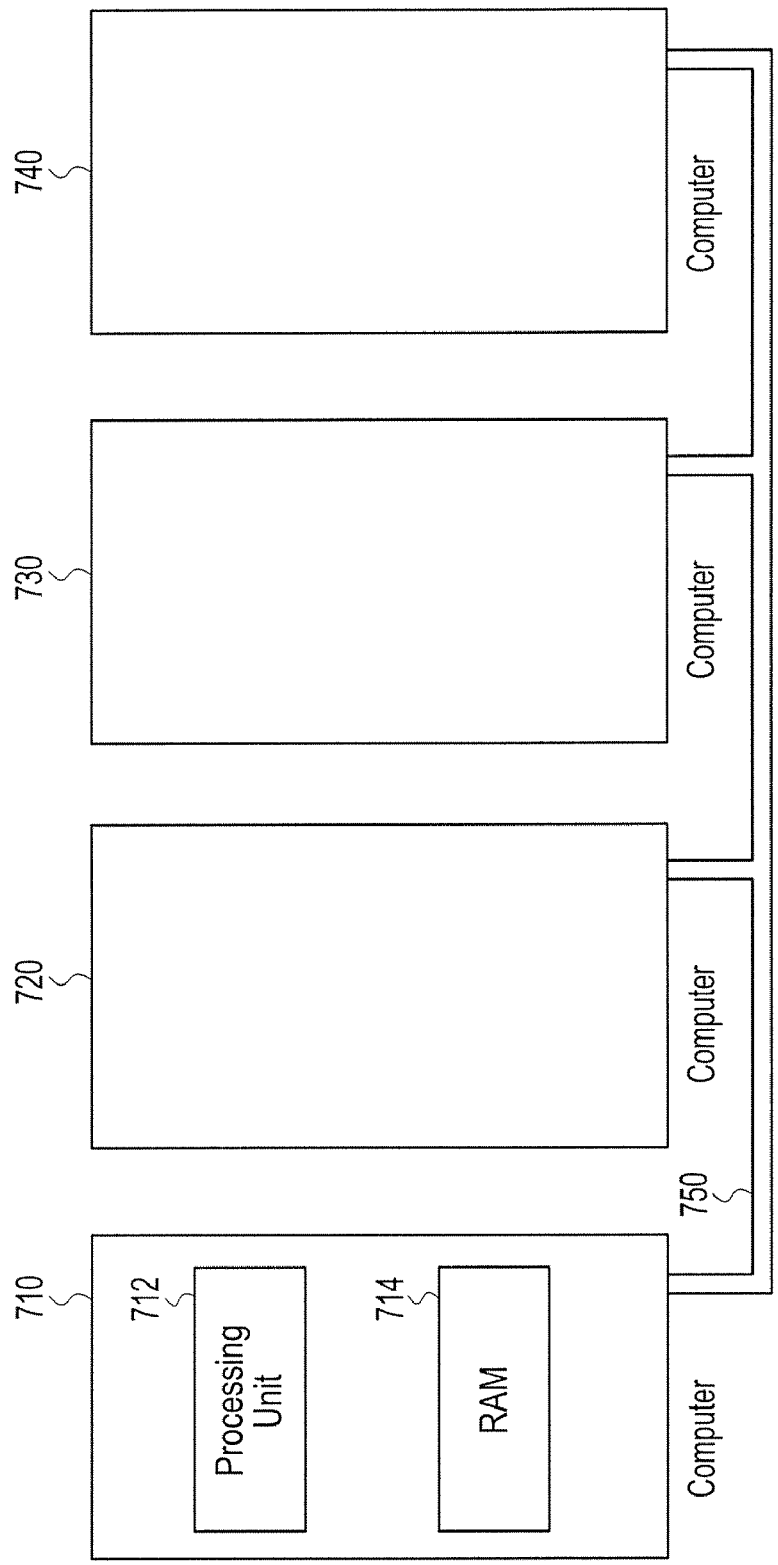
FIG. 7 illustrates the hardware used to generate a model according to an exemplary embodiment of the present invention.

An exemplary process for creating the filtering models is implemented as a collection of software programs that can be run automatically on computer hardware. FIG. 7 shows the hardware necessary for generating the filtering models. A single computer 710 is an example of the hardware necessary to generate the models. The computer 710 comprises a processing unit 712 and memory 714. The memory 714 must be large enough to handle the computations necessary to generate the models. In an exemplary embodiment the models are generated with a cluster of computers 700 comprising computers 710, 720, 730, and 740. Each computer has a processor 712 and memory 714. In an exemplary embodiment each computer 710, 720, 730, and 740 has 4 GB of RAM memory 714 and a Pentium 4 processor 714. The computer cluster 700 is connected together by a Local Area Network 750 and each computer 710, 720, 730, and 740 is running Linux. The filtering models can also be generated on a field programmable gate array or other various hardware systems that process algorithms.

Figure 8:
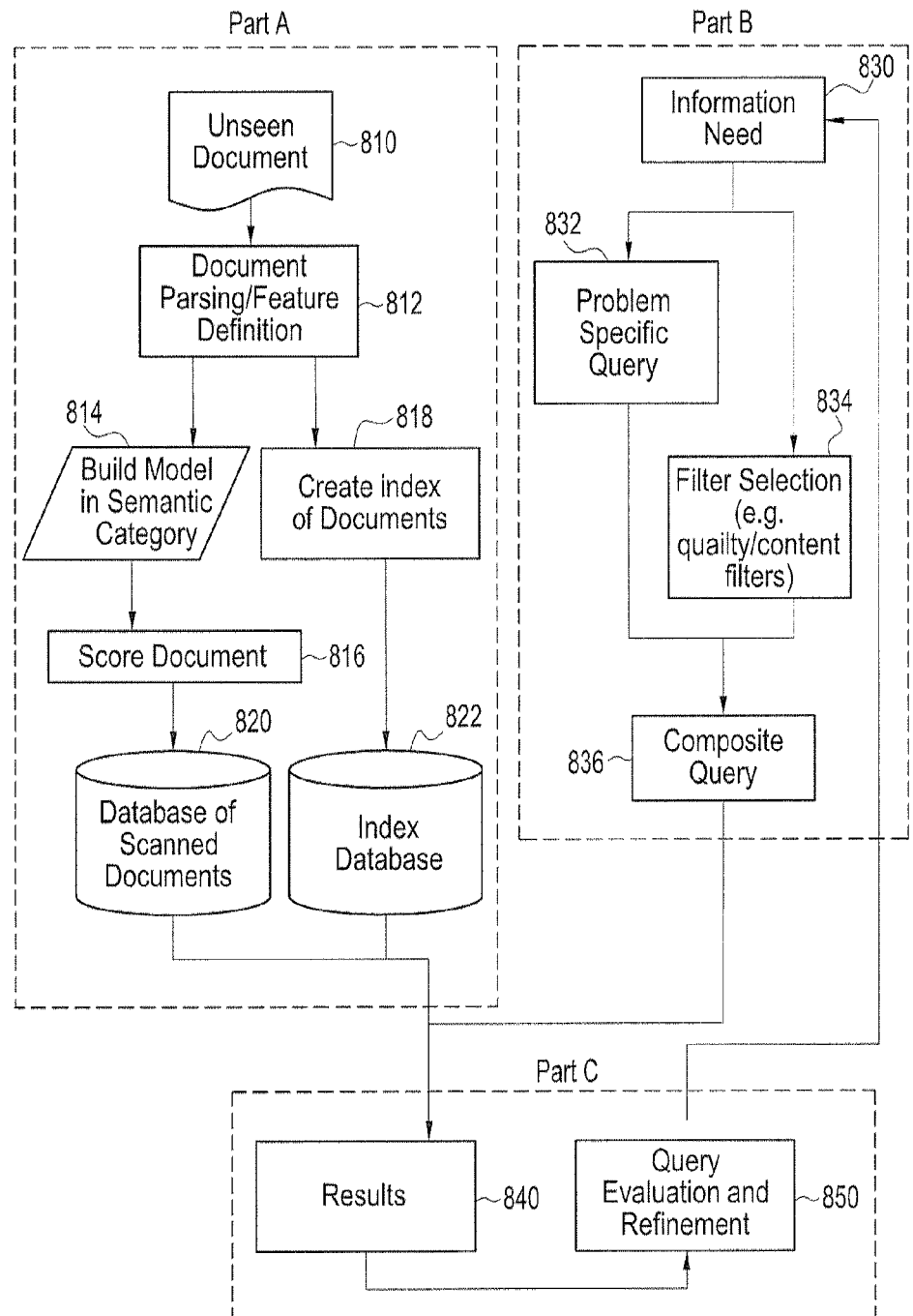
FIG. 8 illustrates the use of the filtering models in an information retrieval system that implements the focusing step according to an exemplary embodiment of the present invention.

FIG. 8 illustrates the use of the filtering models in an information retrieval system that implements an exemplary focusing step of the invention and gives access of the resulting documents to the end user. The system is conceptually divided into three components: Parts A, B, and C.

Component Part A applies the filtering models and stores the results for each document in the document collection so that scores can be retrieved efficiently. An unseen document 810 is subjected to document representation and feature definition at step 812 as defined during document representation 240 and feature modification 250 as described earlier. The process continues by running the processed document against a built model at step 814, scoring the document at step 816, and storing the document in a database of scored documents 820. Part A processes also include the creation of a document index at step 818, which is stored in an index database 822. In a variation of the Part A component, classifications are not pre-computed but are applied in run-time. In another variation the original best model is not applied but a simplified Boolean query is applied to a standard search engine or other database that can give access to the document collection via a Boolean query interface.

Component Part B accepts a user query at step 830 that conveys information about (a) the problem specifics (e.g., the cancer of interest) at step 832, and (b) content/quality requirements (e.g., user wishes to retrieve diagnosis-related documents of high methodological quality only) at step 834. These pieces of information form the composite query 836 submitted to Part A. The user does not need to input the quality requirements as the default for this setting could be high quality documents only. In addition, in certain applications the user would only have a choice to input a query into the system and would not be able to select the quality. In another implementation, the query maybe to returned all documents, but the return documents would be ranked in some way to indicate to the user which documents are considered higher quality than others. The query may be a natural language, Boolean based, or form-field based formulation.

Component Part C receives the returned set of documents 840 that was requested by the user and displays them to the user. This component is also responsible for providing the user with explanations of why the filtering model classified the documents the way it does, and may also receive relevance feedback from the user for evaluation and refinement at step 850.

Figure 9:
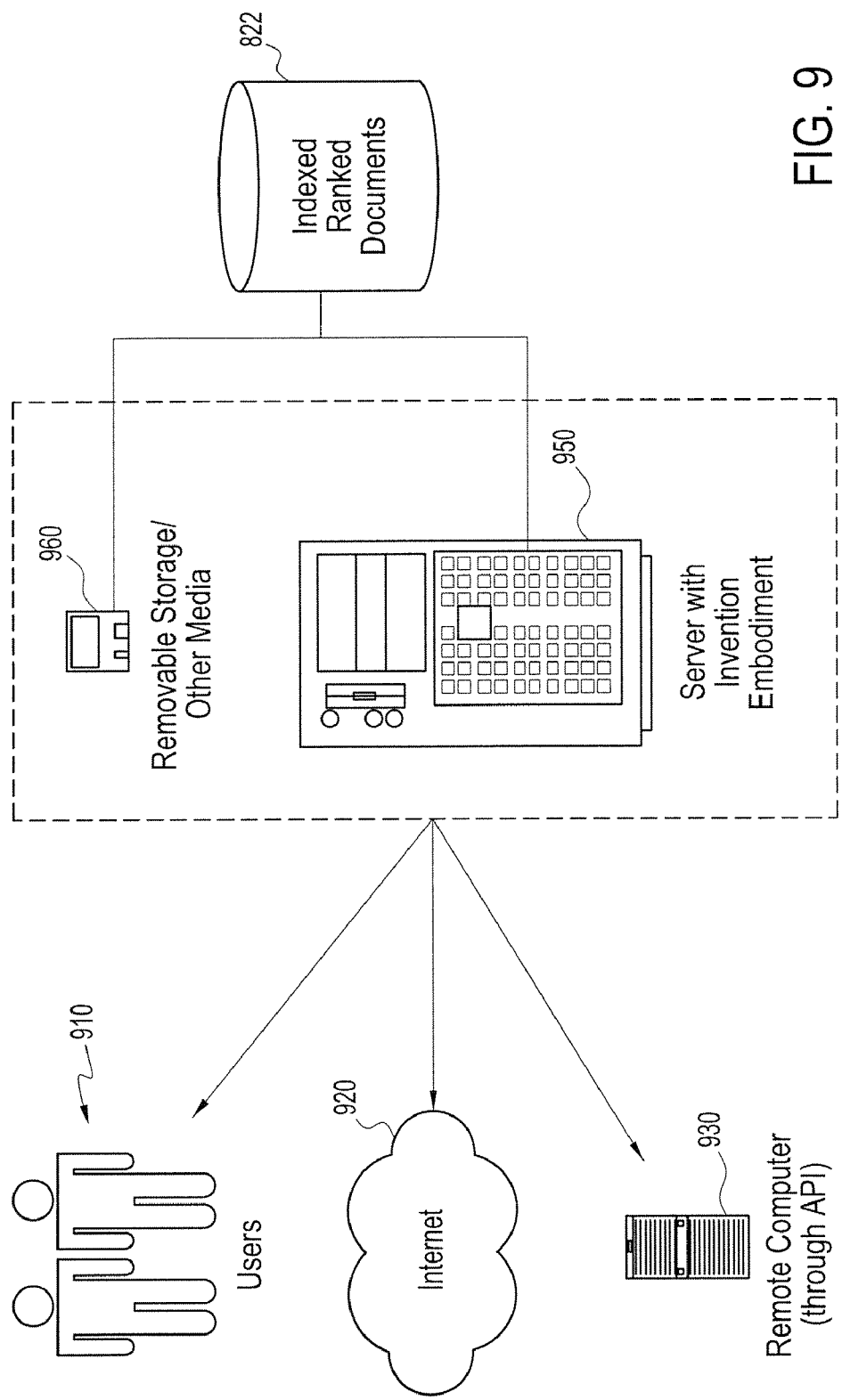
FIG. 9 illustrates application of the invention in a broader context of users by way of the Internet and other remote and/or portable computers according to an exemplary embodiment of the present invention.

FIG. 9 illustrates the application of the invention in the broader context of users 910, the Internet 920, and other remote and/or portable computers 930, without limitation. The invention may reside and/or operate on a server 950 or other media 960, for example. Users 910 may interact directly with the server 950 or other media 960, through the Internet 920, or through an API from a remote computer 930, for example, to obtain information from the indexed classified document results 822 or through documents that are classified at run time. The invention may also reside on an individual computing platform. An exemplary embodiment of the invention is a user 910 performing a search on Google for treatments of colon cancer. A model is selected according to the search terms inputted by the user 910. The selected model has been previously generated using websites containing the search terms to allow for accurate filtering. The model selected is used to identify web pages that are low quality because they contain information on unproven cancer treatment claims. The model would reside on a server 950 or other media 960. The resulting search results are prepared and run through the filtering model on the server 950 or the remote computer 930. The results from the filtering model classifying the web pages are displayed with the results of the search indicating which documents are low quality and which are high quality. The user 910 is able to see the results of the model and the Google search through the internet 920 or a remote computer 930. In another embodiment the server 950 or removable media 960 can be connected to an index of previously classified web pages 822. In this instance the web pages would not need to be run through a model but only the previous classification of the web pages, identified by the Google search, are displayed to the user 910.

The above description and drawings illustrate preferred embodiments which achieve the objects, features, and advantages of the present invention. Although certain advantages and preferred embodiments have been described above, those skilled in the art will recognize that substitutions, additions, deletions, modifications and/or other changes may be made without departing from the spirit or scope of the invention. Accordingly, the invention is not limited by the foregoing description but is only limited by the scope of the appended claims.

The invention claimed is:

1. A computer-based process utilizing a specifically programmed computer for filtering information according to content quality that is organized in documents comprising the steps of:
   A) obtaining a selected set of documents;
   B) labeling each document of the selected set based on content quality with the documents labeled as positive if they match content and quality criteria and labeled as negative if they do not match content and quality criteria;
   C) extracting and representing features from each document in the selected set;
   D) modifying the extracted represented features;
   E) constructing models using pattern recognition algorithms to assign a label to a document;
   F) constructing models for labeling documents based on content quality using pattern recognition algorithms stored in the storage device consisting of the following steps;
      1) dividing the first set of documents into N subsets such that the union of all the subsets is the first set of documents;
      2) choosing at least one pattern recognition algorithm;
         a) instantiating a set of parameters for the pattern recognition algorithm;
            i) processing each of the N subsets comprising the following steps;
               a') defining a first subset and defining a second subset mutually exclusive of the first subset;
               b') training the pattern recognition algorithm to build a model using the first subset and the parameter set;
               c') applying the model to the second subset of documents to obtain labels and scores for each document;
               d') evaluating the labels and scores;
               e') storing the evaluation measure, set of parameters, and current pattern recognition algorithm; and
         b) repeating step 2a) until all appropriate sets of parameters for the pattern recognition algorithm have been applied; and
      3) repeating step 2) until all pattern recognition algorithms have been applied;
      4) aggregating the evaluation measures for the N subsets, the pattern recognition algorithms with the set of parameters;
      5) selecting the parameter set and pattern recognition algorithm with an aggregate evaluation measure that meets a selection criteria;
      6) applying the parameter set and the pattern recognition algorithm identified from step 5) to the first set of documents to build a final model; and
   G) constructing a final model with the appropriate pattern recognition model and associated parameter to assign a label and/or a score to a set of previously unlabeled documents; and
   H) displaying the label and/or score of at least one of the previously unlabeled documents.

2. A process according to claim 1 in step A, wherein the set of documents are chosen using a plurality of different sources.

3. A process according to claim 1 in step C, wherein the step of extracting and representing features from each document in the selected set is performed using a plurality of different methods.

4. A process according to claim 1 in step D, wherein the step of modifying the extracted represented features from each document in the selected set is performed using a plurality of different methods.

5. A process according to claim 1 in step A, wherein the selected set of documents is comprised of web pages.

6. A process according to claim 1 in step A, wherein before obtaining the first set of documents, the first set of documents had been previously labeled by the model.

7. A process according to claim 1 in step A, wherein obtaining the first set of documents is done by a search algorithm.

8. A process according to claim 1 in step B, in which the documents are labeled as positive if they match content and quality criteria and labeled as negative if they do not match content and quality criteria.

9. A process according to claim 8, wherein all positively and negatively labeled documents are presented in the search results.

10. A process according to claim 8, wherein positively labeled documents are presented in the search results.

11. A system using a model to filter documents according to quality comprising:
   A) a storage device;
   B) at least one processor to implement the following steps:
   C) obtaining from the storage device a first set of documents labeled according to content quality;
   D) extracting and representing features from the first set of documents;
   E) modifying the extracted represented features;
   F) constructing models for labeling documents based on content quality using pattern recognitional algorithms stored in the storage device consisting of the following steps;
      1) dividing the first set of documents into N subsets such that the union of all the subsets is the first set of documents;
      2) choosing at least one pattern recognition algorithm;
         a) instantiating a set of parameters for the pattern recognition algorithm;
            i) processing each of the N subsets comprising the following steps;
               a') defining a first subset and defining a second subset mutually exclusive of the first subset;
               b') training the pattern recognition algorithm to build a model using the first subset and the parameter set;
               c') applying the model to the second subset of documents to obtain labels and scores for each document;
               d') evaluating the labels and scores;
               e') storing the evaluation measure, set of parameters, and current pattern recognition algorithm; and
         b) repeating step 2a) until all appropriate sets of parameters for the pattern recognition algorithm have been applied; and
      3) repeating step 2) until all pattern recognition algorithms have been applied;
      4) aggregating the evaluation measures for the N subsets, the pattern recognition algorithms with the set of parameters;
      5) selecting the parameter set and pattern recognition algorithm with an aggregate evaluation measure that meets a selection criteria;
      6) applying the parameter set and the pattern recognition algorithm identified from step 5) to the first set of documents to build a final model; and
   G) obtaining a second set of non-labeled documents related to the first set of documents;
   H) using the final model to label and score the second set of documents according to content quality; and
   I) displaying the label and/or score of at least one of the previously unlabeled documents.

12. A system according to claim 11 in steps C and G, wherein the first and second set of documents are web pages.

13. A system according to claim 11 in step A, further comprising a server wherein the storage device is located on the server.

14. A system according to claim 11 in step B, wherein the at least one processor is programmed to iteratively use the first subset of the first set of documents to instantiate parameters for the models.

15. A system according to claim 11 in step B, wherein the at least one processor is programmed to iteratively use a second subset of the first set of documents to validate the models to select the parameters of the models.

16. A process according to claim 11 in step C in which the documents are labeled as positive if they match content and quality criteria and labeled as negative if they do not match content and quality criteria.

17. A process according to claim 16 wherein all positively and negatively labeled documents are presented in the search results.

18. A process according to claim 16 wherein positively labeled documents are presented in the search results.

19. A process according to claim 11 in step C wherein the set of documents are chosen using a plurality of different sources.

20. A process according to claim 11 in step D wherein the step of extracting and representing features from each document in the selected set is performed using a plurality of different methods.

21. A process according to claim 11 in step E wherein the step of modifying the extracted and represented features from each document in the selected set is performed using a plurality of different methods.

22. A process according to claim 11 in step C wherein the selected set of documents is comprised of web pages.

23. A process according to claim 11 in step C wherein before obtaining the first set of documents, the first set of documents had been previously labeled by the model.

24. A process according to claim 11 in step C wherein obtaining the first set of documents is done by a search algorithm.

25. A process according to claim 11 in step (F)(2) wherein the at least one pattern recognition algorithm accepts as input a row column matrix with numeric cells and outputs a label.

26. A process according to claim 11 in step (F)(2)(a)(i)(d') wherein the evaluation measure may include a plurality of methods that summarize how well the assigned label matches the true label of a document or how well an assigned scores ranks the document in content quality.

27. A process according to claim 11 in steps (F)(2)(a)(i)(d') and 30 (H) wherein the scores may be ranked and a threshold set above or below which the documents are assigned a label.

28. A process according to claim 11 in step (F)(4) wherein aggregation may include a plurality of methods not limited to averaging, majority voting, or other aggregation scheme.

29. A process according to claim 11 wherein the pattern recognition algorithm loop at steps (F)(2) and steps (F)(3), the parameter loop at steps (F)(2)(a) and steps (F)(2)(b), and the subset loop at steps (F)(1) may be interchanged to produce an evaluation measure for the outer loop.

30. A system to estimate performance of a model to filter documents according to quality comprising:
   A) a storage device;
   B) at least one processor to implement the following steps:
   C) obtaining from the storage device a set of documents labeled according to content quality;
   D) extracting and representing features from the set of documents;
   E) modifying the extracted represented features;
   F) constructing models to estimate performance for labeling documents based on content quality using pattern recognition algorithms stored in the storage device consisting of the following steps;
1) dividing the set of documents into N subsets such that the union of all the subsets is the set of documents;
2) processing each of the N subsets comprising the following steps:
   a) defining a first set of documents, a second set of documents, and a third set of documents in the subset;
   b) choosing at least one pattern recognition algorithm;
      i) instantiating a set of parameters for the pattern recognition algorithm;
         a') training the pattern recognition algorithm to build a model using the first set of documents and the parameter set;
         b') applying the model to the second set of documents to obtain labels and scores for each document;
         c') evaluating the labels and scores;
         d') storing the evaluation measure, set of parameters, and current pattern recognition algorithm; and
         e') repeating step i) until all appropriate sets of parameters for the pattern recognition algorithm have been applied; and
   c) repeating step 2b) until all pattern recognition algorithm have been applied;
   d) aggregating the evaluation measures, the pattern recognition algorithms with the set of parameters;
   e) selecting the parameter set and pattern recognition algorithm with an aggregate evaluation measure that meets a selection criteria;
   f) applying the parameter set and the pattern recognition algorithm identified from step e) to the union of the first and second subset to form an intermediate final model;
   g) applying the intermediate final model to the third set of documents to obtain labels and scores for each document;
   h) evaluating the labels and scores;
   i) storing the intermediate evaluation measure;
   j) repeating step 2 until all subsets have been applied; and
3) aggregating the intermediate evaluation measures to form an aggregate evaluation measure; and
4) displaying the aggregate evaluation measure as the estimated performance.

31. A system according to claim 30 in step B, wherein the at least one processor is programmed to apply the validated models to a third subset of the first set of documents, that is mutually exclusive of the first and second subsets to evaluate performance.

32. A system according to claim 30 in step B, wherein the at least one processor is programmed to iteratively apply the validated models to a third subset of the first set of documents, that is mutually exclusive of the first and second subsets to evaluate performance.

33. A process according to claim 30 in step C in which the documents are labeled as positive if they match content and quality criteria and labeled as negative if they do not match content and quality criteria.

34. A process according to claim 30 in step C wherein the set of documents are chosen using a plurality of different sources.

35. A process according to claim 30 in step E wherein the step of modifying the extracted and represented features from each document in the selected set is performed using a plurality of different methods.

36. A process according to claim 30 in step D wherein the step of extracting and representing features from each document in the selected set is performed using a plurality of different methods.

37. A process according to claim 30 in step C wherein the selected set of documents is comprised of web pages.

38. A process according to claim 30 in step (F)(2)(b) wherein the at least one pattern recognition algorithm accepts as input a row column matrix with numeric cells and outputs a label.

39. A process according to claim 30 in steps (F)(2)(b)(i)(d') and (F)(2)(h) wherein the evaluation measure may include a plurality of methods that summarize how well the assigned label matches the true label of a document or how well an assigned scores ranks the document in content quality.

40. A process according to claim 30 in steps (F)(2)(b)(i)(d') and (F)(2)(h) wherein the scores may be ranked and a threshold set above or below which the documents are assigned a label.

41. A process according to claim 30 in steps (F)(2)(d) and (F)(3) wherein aggregation may include a plurality of methods not limited to averaging, majority voting, or other aggregation scheme.

42. A process according to claim 30 wherein the pattern recognition algorithm loop in steps (F)(2)(b) and (F)(2)(c), the parameter loop in steps (F)(2)(b)(i) and (F)(2)(b)(i)(e'), and the subset loop in steps (F)(2) and (F)(2)(j) may be interchanged to produce an evaluation measure for the outer loop.

* * * * *